United States Patent [19]

Davies et al.

[11] Patent Number: 5,322,933
[45] Date of Patent: Jun. 21, 1994

[54] CRYSTAL STRUCTURE OF TGF-BETA-2

[75] Inventors: David R. Davies, Kensington; Sun Daopin, Rockville, both of Md.; Yasushi Ogawa, Pacifica, Calif.; Karl Piez, Chevy Chase, Md.

[73] Assignee: The United States of America as represented by the Secretary of the Department of Health and Human Services, Washington, D.C.

[21] Appl. No.: 879,358

[22] Filed: May 7, 1992

[51] Int. Cl.$^5$ ............................................. A61K 37/00
[52] U.S. Cl. ..................................... 530/399; 530/324
[58] Field of Search .................... 530/416, 356, 399; 514/2, 12, 21

[56] References Cited

U.S. PATENT DOCUMENTS

| | | | |
|---|---|---|---|
| 4,434,094 | 2/1984 | Seyedin et al. | 530/416 |
| 4,627,982 | 12/1986 | Seyedin et al. | 424/549 |
| 4,760,131 | 7/1988 | Sundsmo et al. | 530/356 |
| 4,774,228 | 9/1988 | Seyedin et al. | 514/21 |
| 4,774,322 | 9/1988 | Seyedin et al. | 530/353 |
| 4,806,523 | 2/1989 | Bentz et al. | 514/2 |
| 4,810,691 | 3/1989 | Seyedin et al. | 514/2 |
| 4,816,442 | 3/1989 | McPherson et al. | 514/12 |
| 4,843,063 | 6/1989 | Seyedin et al. | 514/2 |
| 4,950,483 | 8/1990 | Ksander et al. | 424/422 |
| 4,971,952 | 11/1990 | Bentz et al. | 514/12 |
| 5,008,240 | 4/1991 | Bentz et al. | 514/2 |
| 5,024,841 | 6/1991 | Chu et al. | 424/422 |

OTHER PUBLICATIONS

Abstract, F. Inagaki, Cell Struct. Funct., Oct. 1990, 15 (5), pp. 237–243.
Abstract, M. P. Schlunegger et al, Nature, Jul. 30, 1992, 358 (6385), pp. 430–434.
Abstract, M. P. Schlunegger et al, FEBS Lett, May 25, 1992, 303 (1), pp. 91–93.
Abstract, A. T. Danishefsky et al, Biochem. Biophys, Res. Commun., Aug. 31, 1992, 187 (1), pp. 146–151.
Gilliland *Meth Enzymol* 104, 370 1984.
Schlunegger et al. *Experientia* 48, A418, 1992.

*Primary Examiner*—Merrell C. Cashion, Jr.
*Assistant Examiner*—David Lukton
*Attorney, Agent, or Firm*—Birch, Stewart, Kolasch & Birch

[57] ABSTRACT

A composition of crystalline TGF-$\beta$2 is described. The tertiary structure of the protein homodimer determined by X-ray crystallography to 2.1 angstrom resolution is shown. This structure provides data useful in the rational design of drugs to mimic the physiologic properties of proteins of the TGF-$\beta$ family.

3 Claims, 2 Drawing Sheets

CRYSTAL STRUCTURE OF TGF-BETA-2

BACKGROUND OF THE INVENTION

1. Field of the Invention

The invention relates to crystalline TGF-$\beta$2, which can be used as a starting material in any of the methods of use for TGF-$\beta$2 outlined in the patents set forth below, but is particularly useful for the determination of the three-dimensional structure of the TGF-$\beta$2 polypeptide.

The three dimensional structure of TGF-$\beta$2 provides information which has a number of uses; principally related to the development of pharmaceutical compositions which mimic the action of TGF-$\beta$2 or other members of the TGF-$\beta$ family of proteins.

2. Description of the Related Art

Transforming growth factor beta (TGF-$\beta$) belongs to a family of growth factors that structurally related, which consists of at least five isoforms, TGF-$\beta$1 through TGF-$\beta$5, and activins and inhibins. These growth factors are involved in regulation of growth and function of many different cell types. TGF-$\beta$s have been shown to stimulate proliferation of certain cells, such as osteoblasts and normal rat kidney fibroblasts grown on soft agar. However, TGF-$\beta$s inhibit the proliferation of most cell types, such as lymphocytes, fibroblasts, endothelial cells and epithelial cells (1–4). In addition to its regulatory roles in cell proliferation, TGF-$\beta$s are also known to regulate a variety of cellular processes, such as the production of extracellular matrix, chemotaxis, differentiation and morphogenesis. Due to the wide regulatory role of proteins of the TGF-$\beta$ family, there are a number of ongoing clinical studies involving the use of TGF-$\beta$s, for example, to suppress inflammation, promote healing of soft tissue wounds, repair damaged bone and cartilage and to control tumor growth (5).

Despite the general multifunctional regulatory role of TGF-$\beta$s, the mechanism by which TGF-$\beta$s regulate cellular processes is unknown. Recently, significant advances have been made in understanding the roles of the three known types of TGF-$\beta$ receptors in signal transduction. A possibility has been raised that TGF-$\beta$ type II receptor may function as a serine/threonine kinase, based on homology of its amino acid sequence to other such kinase proteins, as a mechanism of signal transduction (6).

TGF-$\beta$s are first expressed in cells as a precursor, which is then thought to be activated through proteolytic cleavage. The mature TGF-$\beta$ has 112 amino acids and forms a functional active homodimer of about 25 kilodaltons molecular weight. The amino acid sequences of TGF-$\beta$ are highly conserved among the human, bovine, porcine, simian, chicken and murine proteins. The high degree of structural conservation among the different species is consistent with the importance of TGF-$\beta$ in regulation of cellular functions.

One route to understanding the function of proteins is to take a structural point of view. Specifically, one determines the 3-D structure of a protein and inquires as to how the structure relates to function. In the case of TGF-$\beta$, the protein is actually one of a large family of similar proteins. It is also known that different forms of TGF-$\beta$ display slightly different affinities to their receptors and this differential binding onto the receptors is regulated according to tissue type, cell type which in turn regulates the cell proliferation. Thus it is critical to understand the structural differences between different forms of TGF-$\beta$s in order to reveal their differences in biological function.

The following U.S. Patents, disclosing material relating to either compositions or methods of use for TGF-$\beta$ or TGF-$\beta$2, have issued. All are hereby incorporated by reference.

| U.S. Pat. No. | issued | subject matter |
| --- | --- | --- |
| 4,434,094 | 2/28/84 | partially purified TGF-$\beta$ |
| 4,627,982 | 12/9/86 | OFE, partially pure OIF |
| 4,760,131 | 7/26/88 | Collagen/heparin gel containing platelet releasates for wound healing |
| 4,774,228 | 9/27/88 | TGF-$\beta$2 for promoting connective tissue deposition |
| 4,774,322 | 9/27/88 | pure TGF-$\beta$ |
| 4,806,523 | 2/21/89 | TGF-$\beta$ for immune modulation |
| 4,816,442 | 3/2/89 | TGF-$\beta$2 inhibition of tumor growth |
| 4,810,691 | 3/7/89 | TGF-$\beta$2 for promoting cell proliferation |
| 4,843,063 | 6/27/89 | TGF-$\beta$ for local/systemic bone repair |
| 4,950,483 | 8/21/90 | Collagen/heparain sponge containing a synergistic combination of TGF-$\beta$ and FGF |
| 4,971,952 | 11/20/90 | Method for treating inflammation |
| 5,008,240 | 4/16/91 | Method for treating inflammation |
| 5,024,84 | 11/16/91 | Collagen wound healing matrices and process for their production |

SUMMARY OF THE INVENTION

The essence of the invention resides in the obtaining of crystals of TGF-$\beta$2 of sufficient quality to determine the three dimensional (tertiary) structure of the protein by X-ray diffraction methods. Obtaining such crystals is in fact very much an unexpected result. It is well known in the protein crystallographic art that obtaining crystals of quality sufficient for determining the structure of the polypeptide of members of the TGF-$\beta$ family of proteins has not been achievable until the crystallization of TGF-$\beta$2, disclosed in the present application.

Accordingly, one object of the present invention is to provide crystals of sufficient quality to obtain a determination of the three-dimensional structure of TGF-$\beta$2 to high resolution, preferably to the resolution of 2.1 angstroms.

The value of the crystals of TGF-$\beta$2 extends beyond merely being able to obtain a structure for TGF-$\beta$2 alone. The knowledge obtained concerning TGF-$\beta$2 can be used to model the tertiary structure of related proteins. For example, the structure of renin has been modelled using the tertiary structure of endothiapepsin as a starting point for the derivation (7). Furthermore, current methods of tertiary structure determination that do not rely on X-ray diffraction techniques and thus do not require crystallization of the protein, such as NMR techniques, are made much simpler if a model of the structure is available for refinement using the additional data gathered by the alternative technique. Thus, knowledge of the tertiary structure of TGF-$\beta$2 provides a window to the structure of the other members of the TGF-$\beta$ family of proteins, including the various species of TGF-$\beta$, the inhibins, activins and Vg-1 protein. Thus, the crystals of TGF-$\beta$2 provide a starting point for investigation into structure of all of these proteins.

Accordingly, a second object of the present invention is to provide a starting material for use in the determination of the structure of other members of the TGF-β family of proteins.

The knowledge of the structure of the TGF-β family of proteins provides a means of investigating the mechanism of action of these proteins in the body. For example, binding of these proteins to various receptor molecules can be predicted by various computer models. Upon discovering that such binding in fact takes place, knowledge of the protein structure then allows chemists to design and attempt to synthesize small molecules which mimic the functional binding of the TGF-β-family protein to the receptor. This is the method of "rational" drug design.

Accordingly, a third object of the invention is to provide material which is a starting material in the rational design of drugs which mimic the action of the TGF-β family of proteins.

DETAILED DESCRIPTION OF THE INVENTION

A. Structure Determination

Figure 1:
FIG. 1 shows a ribbon drawing of the tertiary structure of the two sub-units of the TGF-β2 protein, which traces the path of the peptide backbone and emphasizes the α-helix and β-sheet elements of the structure.

Even though this family of growth factors comprises many proteins, none of the x-ray crystallographic structure is known. Other investigators have attempted the crystallization of TGF-β and related proteins, such as activin and inhibin, without success. It is well known that the processes for obtaining crystals of particular proteins are individual to each protein. We have chosen TGF-β2 as the model protein and have successfully crystallized it from a solution of 20% polyethyleneglycol (PEG) 200, 100 mM sodium acetate, pH 4.2, using the "hanging drop" method known in the art (8). In all crystallizations described herein the initial concentration of protein was 10 mg/ml and the initial drop size was 10 μl.

TGF-β2 was obtained by purification from medium conditioned by culture of a Chinese hamster ovary cell line secreting recombinant simian TGF-β2. Conditioned medium was concentrated by ultrafiltration and crystalline urea was added to a final concentration of 6M. The pH wa adjusted to 2 by adding HCl to activate the TGF-β2. The medium was then applied to a cation exchange column (Whatman CM52) equilibrated with 50 mM sodium acetate, 50 mM NaCl, 6M urea, pH 4.6. TGF-β2 was eluted with a linear 50-600 mM NaCl gradient. The fraction containing TGF-β2 was applied to a C18 reverse phase HPLC column and TGF-β2 was eluted with a linear gradient of acetonitrile in 0.1% trifluoroacetic acid (TFA). TGF-β2 containing fractions were rechromatographed by C18 reverse phase HPLC as above. Finally, TGF-β2 was applied to a C18 reverse phase HPLC column and eluted with a linear gradient of ethanol in 20 mM HCl.

The best crystals diffracted to about 2.0 angstrom in resolution and are suitable for x-ray crystallographic structure determination.

Two forms of TGF-β2 crystals were obtained. The first form was obtained from 20% PEG 600 in 30 mM $CaCl_2$, pH 4.2 and precipitated as tetragonal crystals of space group $P4_12_12$ (or the enantiomorphic group $P4_32_12$) with unit cell dimensions a=b=55.8 angstroms, c=70.8 angstroms. These crystals provided diffraction data at 2.8 angstrom resolution. The second form of TGF-β2 crystal was obtained from 20% PEG 200, 100 mM sodium acetate, pH 4.2 and precipitated as trigonal crystals of space group $P3_22_1$ with unit cell dimensions a=b=60.6 angstroms, c=75.3 angstroms. One set of native data was collected to 2.1 angstrom resolution from these crystals.

Subsequently, the multiple isomorphous replacement method (MIR method for short) was used to determine the initial phases. Heavy atoms were diffused into the trigonal crystals of TGF-β2, but can in principle also be diffused into the tetragonal crystals as well. During the heavy atom derivative search, three compounds are found to produce the interpretable derivatives. These are uranyl sulfate, iodine and mercurous oxide. The data for the three derivatives of the trigonal crystals were collected to 2.8, 3.2 and 3.2 angstrom resolution respectively. The initial phases were calculated with these three derivatives to 3.2 angstrom resolution and the electron density map was interpretable in most of places. A partial chain tracing was carried out using this initial electron density map. Having the partial structure, the phases were extended to 2.8 angstrom resolution by combining the MIR and model phases. The subsequent phase extended map was shown better than the original map. This allowed the complete chain trace with the exception from residue 91 to 96, where the density was very weak. The structure refinement was done using program TNT (9) and the final resolution of the structure was extended to 2.1 angstrom during the refinement. The refined structure contains all the amino acid residues, from 1 to 112, together with 32 solvent molecules and the crystallographic residual R factor is 0.172. The atomic coordinates of the structure will be deposited in the Brookhaven Protein Databank. The data set of these atomic coordinates for the TFG-β2 protein is hereby incorporated by reference.

We were also able to obtain somewhat poorer crystals of TGF-β1, which are able to diffract to about 4 angstroms. TGF-β1 was purified from bovine bone. Metatarsals and metacarpals (100 pieces) were obtained fresh from a slaughterhouse and separated from soft tissue. The cleaned bone was then ground into powder, washed with water and demineralized in 0.5N HCl. The demineralized bone powder was extracted with 4M guanidine HCl, 10 mM disodium EDTA, pH 6.8. The extract was fractionated through a Sephacryl S-200 gel filtration column (25.2×74 cm) in the guanidine-/EDTA buffer. After passage of the TGF-β fraction through an Amicon GH 25 desalting column to exchange the buffer to 50 mM sodium acetate, 10 mM NaCl, 6M urea, pH 4.6, the TGF-β fraction was applied to a carboxymethyl cellulose column (Whatman CM52, 2.5×36 cm) equilibrated with 50 mM sodium acetate, 70 mM NaCl, 6M urea, 1% isopropanol, pH 4.6. TGF-β was eluted with a linear gradient of 70-600 mM NaCl in the same buffer. Fractions containing TGF-β were identified by SDS-PAGE. TGF-β1 eluted slightly after TGF-β2. TGF-β1 fractions were pooled and applied to a S-Sepharose cation exchange column equilibrated with 20 mM HEPES, 10 mM NaCl, 6M urea, 1% isopropanol, pH 9.0. TGF-β1 was eluted with a 10-400 mM NaCl gradient in the same buffer and further fractionated by C18 reverse phase HPLC, using a linear gradient as follows:

Buffer A: 0.1% TFA
Buffer B: 90% acetonitrile in 0.1% TFA
gradient: 32-62% buffer B, slope=1% buffer B/min
TGF-$\beta$1 so purified was estimated to be 99% pure by SDS-PAGE Hexagonal crystals of TGF-$\beta$1 were obtained from 20% PEG 600 in approximately 10 mM Tris pH 7.7, 0.1M $CaCl_2$. The crystals formed in space group $P6_122$ or the enantiomorphic space group $P6_522$ and had unit cell dimensions a=b=152.3 angstroms, c=72.2 angstroms. Heavy atom replacement can be performed for these crystals as described above for the crystals of TGF-$\beta$2.

B. Description of the Tertiary Structure of TGF-$\beta$2

Figure 2:
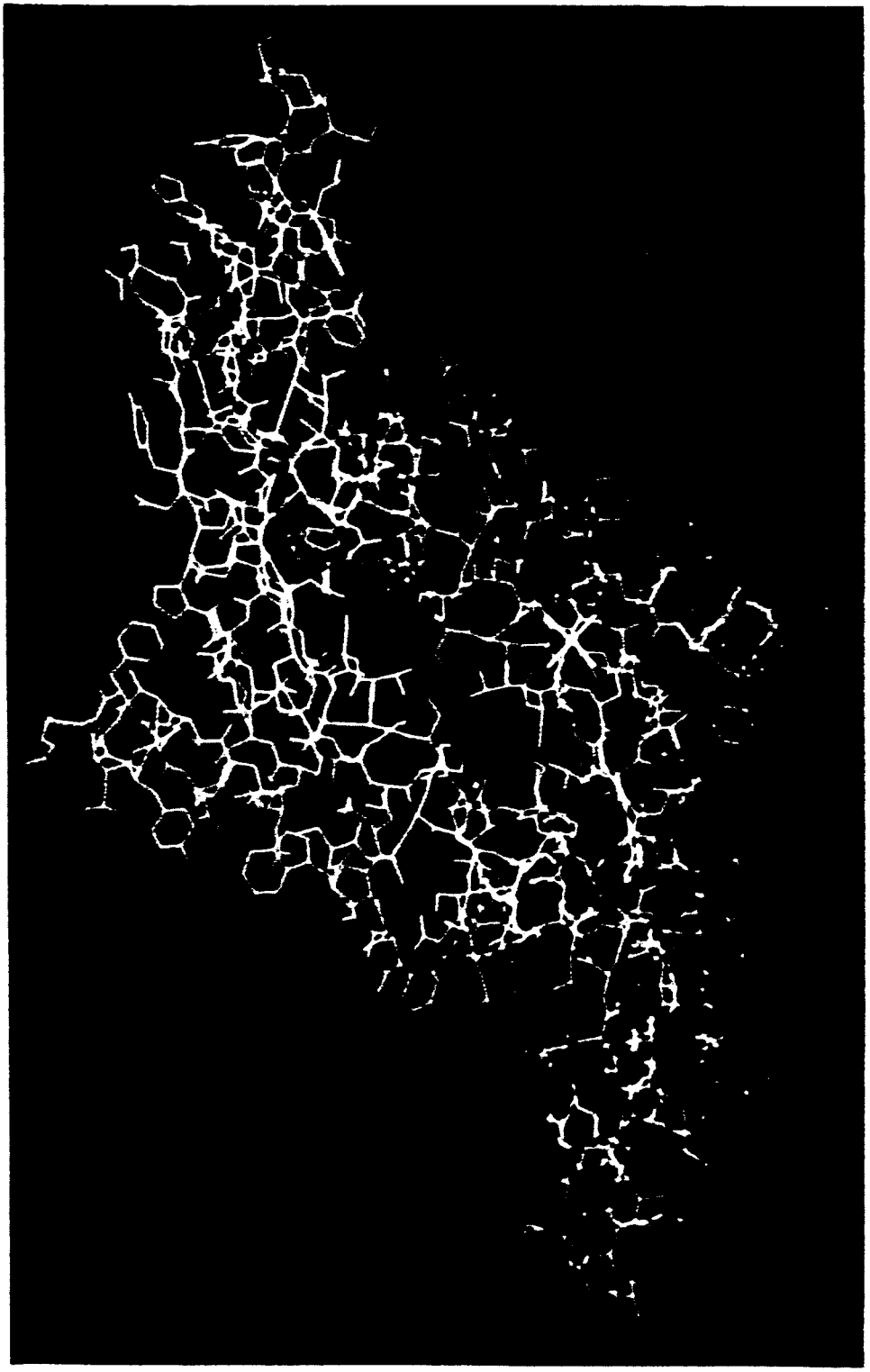
FIG. 2 shows the entire structure of the TGF-β2 protein molecule including the side chain atoms.

FIG. 1 shows the ribbon structure of the TGF-$\beta$2 protein. FIG. 2 shows the complete structure of the polypeptide, including the side chains. The figures were drawn using the RIBBON program of Carson (10). The crystal structure reveals TGF-$\beta$2 in a dimeric form having two 112 amino acid monomers connected through a disulfide link. The two monomers are structurally identical and are related by a two fold axis. There are nine disulfide bonds in the dimer of TGF-$\beta$2. Among them, four are intra-monomeric disulfides connecting residue 7-16, 15-78, 44-109 and 48-111 in each monomer. The last one is aninter-monomeric disulfide connecting between residue 77 of the two monomers.

The major secondary structure elements of TGF-$\beta$2 consists of two alpha helices and five beta sheets. The first alpha helix has only one turn and is from residue 4 to 8. The second helix has three turns and is from residue 58 to 68. The beta sheets are the following:

| | |
|---|---|
| sheet 1 | residue 15-19 pair with residue 42-46 |
| sheet 2 | residue 20-23 pair with residue 37-40 |
| sheet 3 | residue 77-80 pair with residue 109-112 |
| sheet 4 | residue 82-84 pair with residue 104-106 |
| sheet 5 | residue 85-91 pair with residue 96-102 |

All are anti-parallel beta sheets.

The tertiary structure is made of a dimer of two identical 112 amino acid polypeptide chains related by a two fold axis. The two monomers are very intimately associated with most of the hydrophobic residues aligning in the inter-monomeric interface.

Using the structure of TGF-$\beta$2 described above to provide constraints should allow the refinement of the (approximately 4 angstrom resolution) data we have obtained thus far from the hexagonal crystals of TGF-$\beta$1, thus providing a clearer picture of the tertiary structure of that protein as well.

The above description is meant to illustrate, rather than limit the scope of the invention. The invention being thus described, certain variations in the materials or methods employed in performing the invention will be obvious to one skilled in the art. For example, the amino acid sequence of the TGF-$\beta$ protein can be varied by mutation, derivatization or by use of a different source of the protein. Such sources may include human or other mammalian species and may include bone tissue or cell cultures expressing TGF-$\beta$ proteins from recombinant plasmids. Any such obvious variation is to be considered within the scope of the invention.

LITERATURE CITED

The following references are cited above. The entire contents of each of these references are hereby incorporated by reference.

1. M. B. Sporn and A. B. Roberts, Cell Regulation 1:875-882 (1990)
2. M. B. Sporn and A. B. Roberts, JAMA 262:938-941 (1989)
3. M. B. Sporn and A. B. Roberts, in "Peptide Growth Factors and Their Receptors I", chapter 8, c. 1990 by Springer-Verlag.
4. J. Massague, Annu. Rev. Cell Biol. 6:597-641 (1990)
5. "Transforming Growth Factor-Bs, Chemistry, Biology, and Therapeutics", Karl A. Piez, Michael B. Sporn, eds. Annals of The New York Academy of Sciences, vol. 593 (1990)
6. H. Y. Lin et al., Cell 68:1-20 (1992)
7. T. Blundell et al., Nature 304:273-275 (1983)
8. G. L. Gilliland and D. R. Davies, Meth. in Enzymol. 104:370-381 (1984)
9. D. E. Tronrud et al., Acta Cryst. A43:489-503 (1987)
N. Carson, J. Mol. Graphics 4:121-122 (1986)

What is claimed is:

1. A composition consisting essentially of TGF-$\beta$ protein in crystalline form, wherein said TGF-$\beta$ is TGF-$\beta$1 or TGF-$\beta$2.

2. A composition which comprises TGF-$\beta$2 polypeptide molecules arranged in a crystalline manner in a space group $P4_12_12$ or $P4_32_12$, so as to form a unit cell of dimensions a=b=55.8 angstroms, c=70.8 angstroms and which effectively diffracts X-rays for determination of the atomic coordinates of the TGF-$\beta$2 polypeptide to a resolution of about 2.9 angstroms.

3. A composition which comprises TGF-$\beta$1 polypeptide molecules arranged in a crystalline manner in a space group $P6_122$ or $P6_522$, so as to form a unit cell of dimensions a=b=152.3 angstroms, c=72.2 angstroms, which effectively diffracts X-rays for determination of the atomic coordinates of the TGF-$\beta$1 polypeptide to a resolution of about 4 angstroms.

* * * * *